United States Patent [19]

Houlihan

[11] 4,036,855
[45] July 19, 1977

[54] PHTHALIDES AND PROCESS FOR PREPARING SAME

[75] Inventor: William J. Houlihan, Mountain Lakes, N.J.

[73] Assignee: Sandoz, Inc., E. Hanover, N.J.

[21] Appl. No.: 626,784

[22] Filed: Oct. 29, 1975

Related U.S. Application Data

[60] Division of Ser. No. 409,923, Oct. 26, 1973, Pat. No. 3,943,147, which is a continuation-in-part of Ser. No. 342,879, March 19, 1973, abandoned, which is a continuation-in-part of Ser. No. 333,499, Feb. 20, 1973, abandoned.

[51] Int. Cl.$^2$ .................... C07D 307/87; A01N 9/28
[52] U.S. Cl. ............................. 260/343.3 R; 424/279
[58] Field of Search ................................ 260/343.3 R

[56] References Cited

U.S. PATENT DOCUMENTS 2,855,395  10/1958  Wheeler et al. .................... 71/88

Primary Examiner—Anton H. Sutto
Attorney, Agent, or Firm—Gerald D. Sharkin; Robert S. Honor

[57] ABSTRACT

Imidazo isoindoles, e.g. 5-(p-chlorophenyl)-5-hydroxy-2,3-dihydro-5H-imidazo[2,1a]isoindol, may be prepared by treating a corresponding 2-benzoyl benzoic acid with a substituted ethylene diamine, and treating a resulting intermediate first with concentrated acid and then with base. The products are active as anorexic agents.

8 Claims, No Drawings

PHTHALIDES AND PROCESS FOR PREPARING SAME

This is a division of application Ser. No 409,923 filed Oct. 26, 1973 now U.S. Pat. No. 3,943,147, said parent application being a continuation-in-part of Ser. No. 342,879 filed Mar. 19, 1973, now abandoned, which in turn was a continuation-in-part of application Ser. No. 333,499 filed Feb. 20, 1973, now abandoned.

This invention pertains to a process for preparing imidazo isoindoles of the formula

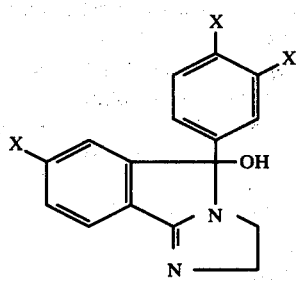
(I)

where each X independently represents H or halo of atomic weight 19 to 36.

The compounds of formula (I) may be prepared according to the process of this invention in a stepwise process by first treating a benzoyl benzoic acid of the formula

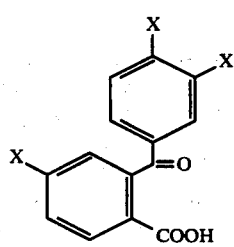
(II)

in inert organic solvent with a substituted ethylene diamine of the formula

(III)

$$H_2N-CH_2CH_2-\overset{H}{N}-SO_2R$$

to provide an intermediate compound of the formula

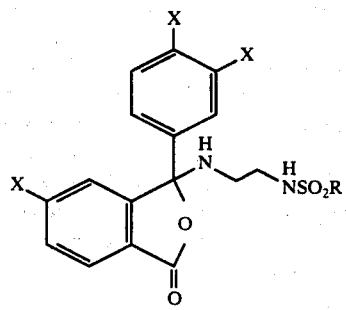
(IV)

where
X is as defined above,

R represents lower alkyl, i.e. alkyl of 1 to 5 carbon atoms, e.g. methyl, ethyl, isopropyl and the like, or

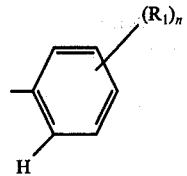

where
$R_1$ represents H, straight chain lower alkyl having 1 to 3 carbon atoms, e.g. methyl and ethyl, or halo or atomic weight 35 to 80, and
$n$ is 1 or 2,
$SO_2R$ preferably representing tosyl.

Inert solvents such as aromatic hydrocarbons, e.g. benzene and toluene, hydrocarbons such as octane, or dioxane, and the like may be used for the reaction. The temperature of the reaction mixture may be about 60°-125°C., more preferably about 75°-115° C., conveniently at the reflux temperature of the system. Toluene is the preferred solvent. The reaction may be performed conveniently in 2-24 hours.

The intermediate compound is then converted in a second step to a tautomer of a compound of the formula (I) (designated compounds (V))

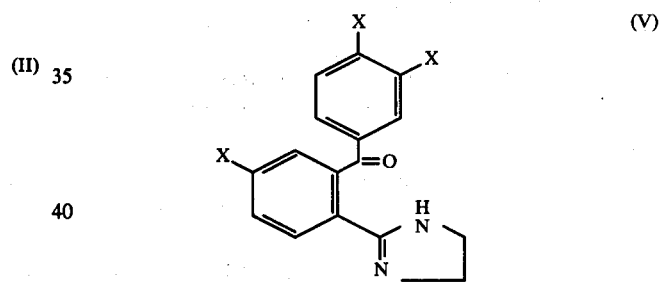
(V)

in acid addition salt form, where X is as defined above by treatment of said intermediate with concentrated sulfuric acid or phosphoric acid, particularly 85-100% sulfuric acid or 85-100% phosphoric acid, preferably 90-98% sulfuric acid.

This step of the reaction may be performed in the absence of a solvent although it will be understood that excess acid is preferably utilized and it essentially acts as solvent during the reaction. The temperature of the reaction mixture is maintained at about 60°-95°C., preferably about 70°-90°C., more preferably about 75°-85°C. for about ½ to 6 hours. It should be understood that the product (V) may also be obtained according to the above process at about room temperature (25°C.) but that longer reaction times, e.g. 24 hours, are desired in that circumstance. The product (I) may be readily recovered by treating the resulting reaction mixture containing compound (V) as the salt with base using conventional basification techniques.

The intermediate compounds (IV) are novel and represent an additional aspect of this invention. It should be understood that they may be recovered and utilized as indicated above, or they may alternatively be treated with the acid without separation from the reaction medium obtained in the first step of the reaction set out above to obtain the desired products.

Compounds (I), (IV) and (V) are recovered by conventional techniques such as filtration and recrystallization.

Compounds of the formulae (II) and (III) are known and may be prepared according to methods disclosed in the literature.

The compounds of formula (I) are known anorexic agents and may be utilized as indicated in the art for the treatment of anorexia.

EXAMPLE 1

5-(4-chlorophenyl)-5-hydroxy-2,3-dihydro-5H-imidazo[2,1a]isoindole

Step 1.
3-(p-chlorophenyl)-3-[2-(4-methylphenylsulfonylamino)ethylaimno]phthalide To a flask equipped with a Dean-Stark water separator is charged 500 ml. of toluene, 24.0 g. (0.10 mole) of 2-(p-chlorobenzoyl) benzoic acid and 21.4 g. (0.10 mole) of N-(2-aminoethyl)-4-methylbenzene sulfonamide. The mixture is stirred and refluxed until the water level in the separator is constant. The reaction is then allowed to cool to room temperature and the resultant solid is filtered off, washed with 100 ml. of toluene and dried to give the above named phalide; m.p. 177°–179° C.: infrared (KBr), peaks at 3.00, 3.09, 3.37, 3.42, 3.48, 5.76, 6.25, 6.71, 7.42, 8.58, 9.12, 9.90, 11.45, 12.80, 13.70, 17.30 and 18.20μ; ultraviolet (95% ethanol) maximum at 226 mμ ($E_{1cm}^{1\%}$ 637), 257 mμ (shoulder); N.M.R. (pyridine- $d_6$) δ 2.22 ($CH_3$), 3.57(4H, $NCH_2Ch_2N$ unresolved multiplet).

Analysis: Calculated for $C_{23}H_{21}ClN_2O_4S$: C,60.4; H, 4.6; N, 6.1; Cl, 7.8; S 7.0. Found: C,60.2; H,4.9; N, 6.1; Cl 7.7; S, 7.7.

Step 2.
5-chlorophenyl)-5-hydroxy-2,3-dihydro-5H-imidazo[2,1a] isoindole

To 135 gms. of 96% sulfuric acid is added with stirring over a period of 5 minutes 50 gms. of 3-(p-chloropheny)-3-[2-(4-methyl-phenylsulfonylamino)ethylanimo]phthalide. The temperature is raised to about 85° C. and is maintained for 1.5 hours. The resulting red solution is cooled to 30° C. and added dropwise with mixing and cooling to 250 milliters of water. Temperature during this dilution is about 40° C. After the addition is complete the aqueous solution is stirred at 10° C. for 30 minutes and then treated with 220 milliliters of 28–30% ammonia by dropwise addition while the temperature is maintained at 25° C. The resulting mixture is stirred for one-half hour and solids are collected by vacuum filtration. The filter cake is washed with water and then acetone ad recrystallized from dimethyl formamide to yield 5-(4-chlorophenyl)- 5-hydroxy-2,3--dihydro-5H-imidazo-[2,1a]isoindole; m.p. 201°–203° C.

When the above two steps are carried out and place of 2-(p-chlorobenzoyl)benzoic acid there is used a. 2-(3,4-dichlorobenzoyl) benzoic acid,
b. 2benzoyl benzoic acid,
c. 2-(3-fluoro benzoyl) benzoic acid,
d. 4-chloro-2-(p-chlorobenzoyl) benzoic acid, or
e. 2-(4-fluorobenzoyl) benzoic acid
there is obtained a. 5-(3,4-dichlorophenyl)-5-hydroxy-2,3-dihydro-5H-imidazo[2,1a]isoindole,
b. 5-phenyl-5-hydroxy-2,3-dihydro-5H-imidazo[2,1a]isoindole,
c. 3-(3-fluorophenyl)-5-hydroxy-2,3-dihydro-5H-imidazo[2,1a]isoindole,
d. 7-chloro-5-(4-chlorophenyl)-5-hydroxy-2,3-dihydro-5H- imidazo[2,1a]isoindole, or
e. 3-(4-fluorophenyl)-5-hydroxy-2,3-dihydro-5H-imidazo[2,1a]isoindole, respectively, through the corresponding phthalide intermediate a. 3-(3,4-dichlorophenyl)-3-[2-(4-methylphenyl sulfonylamino) ethylamino]phthalide; m.p. 167°–170° C,
b. 3-[2-(4-methylphenylsulfonylamino)ethylamino]-3-phenyl phthalide; m.p. 157°–169° C,
c. 3-(3-fluorophenyl)-3-[2-(4-methylphenyl sulfonylamino) ethylamino]phthalide;
d. 5-chloro-3-(4-chlorophenyl)-3-[2-(4-methylphenylsulfonylamino)ethylamino]phthalide, or
e. 3-(4-fluorophenyl)-3-[2-(4-methylphenyl sulfonylamino) ethylamino]phthalide; m.p. 153°–155° C, respectively.

When the above two-step process is carried out and in the first step in place of N-(2-aminoethyl)-4-methylbenzene sulfonamide there is used N-(2-aminoethyl)-4-chlorobenzene sulfonamide, the identical products are again obtained.

EXAMPLE 2.

5-(4-chlorophenyl)-5hydroxy-2,3-dihydro-5H-imidazo[2,1a]isoindole

Step 1

To a flask equipped with a Dean-Stark separator is charged 1 liter of toluene, 48 gms. of 2-(p-chlorobenzoyl) benzoic acid, and 42.8 gms. of N-(2-aminoethyl)-4-methylbenzene sulfonamide. The mixture is stirred and refluxed for 2½ hours during which time 3.4 mls. of water separates. The product crystallizes out of the reaction mixture on cooling. It is filtered, then recrystalized from hot tetrahydrofuran and hexane (about 2:1) to give a white crystalline solid having the physical characteristics shown above for the product of Example 1, Step 1.

Step 2

The intermediate prepared above (5 gms.) is dissolved in 13.5 gms. of 96% sulfuric acid and stirred at 65° C. for 1½ hours. The resulting red solution is cooled to 30° C., then added dropwise with mixing and cooling to 25 mls. of water. The temperature rises to 40° C. during this dilution, and a white precipitate results. The suspension is neutralized with 28–30% ammonium hydroxide by dropwise addition with cooling to produce a paste-like solid. This paste is crystallized by treatment with acetone. The mixture is filtered and the collected solids recrystallized from N,N,dimethyl formamide. The white crystalline solid is washed with acetone, then dried to yield 5-(4-chlorophenyl)-5-hydroxy-2,3-dihydro-5H-imidazo[2,1a]isoindole.

What is claimed is:
1. A compound of the formula

-continued

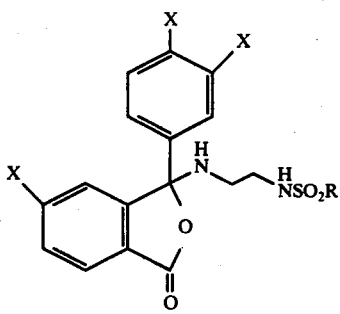

where
X represent H or halo of atomic weight 19 to 36, and
R represents lower alkyl, or

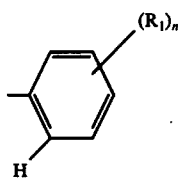

where
R₁ represents H, straight chain lower alkyl having 1 to 3 carbon atoms, or halo of atomic weight 35 to 80, and n is 1 or 2.

2. A compound according to claim 1 which is 3-(p-chlorophenyl) -3-[2-(4-methylphenylsulfonylamino)ethylamino]phthalide.

3. A compound according to claim 1 which is 3-(3,4-dichlorophenyl) -3-[2-(4-methylphenylsulfonylamino)ethylamino]phthalide.

4. A compound according to claim 1 which is 3-[2-(4-methylphenylsulfonylamino) ethylamino]-3-phenyl phthalide.

5. A compound according to claim 1 which is 3-(3-fluorophenyl)-3-[2-(4-methylphenylsulfonylamino)ethylamino]phthalide.

6. A compound according to claim 1 which is 5-chloro-3-(4-chlorophenyl)-3-[2-(4-methylphenylsulfonylamino)ethylamino]phthalide.

7. A compound according to claim 1 which is 3-(4-fluorophenyl)- 3-[2-(4-methylphenylsulfonylamino)ethylamino]phthalide.

8. A process for preparing a compound of claim 1 which comprises treating a compound of the formula

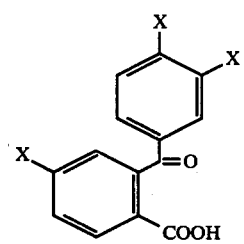

with a compound of the formula

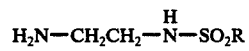

in inert solvent at a temperature of about 75°–115° C. where X and R are as defined in claim 1.

* * * * *